(12) United States Patent
Hayashida et al.

(10) Patent No.: US 12,334,211 B2
(45) Date of Patent: Jun. 17, 2025

(54) STORAGE MEDIUM, DIAGNOSIS SUPPORT APPARATUS AND DIAGNOSIS SUPPORT METHOD

(71) Applicant: FIXSTARS CORPORATION, Tokyo (JP)

(72) Inventors: Tetsu Hayashida, Tokyo (JP); Noriyuki Futatsugi, Tokyo (JP); Yasuhiko Shiota, Tokyo (JP)

(73) Assignee: FIXSTARS CORPORATION, Tokyo (JP)

( * ) Notice: Subject to any disclaimer, the term of this patent is extended or adjusted under 35 U.S.C. 154(b) by 428 days.

(21) Appl. No.: 17/796,694

(22) PCT Filed: Jan. 28, 2021

(86) PCT No.: PCT/JP2021/002960
§ 371 (c)(1),
(2) Date: Aug. 1, 2022

(87) PCT Pub. No.: WO2021/153648
PCT Pub. Date: Aug. 5, 2021

(65) Prior Publication Data
US 2023/0057933 A1   Feb. 23, 2023

(30) Foreign Application Priority Data
Jan. 31, 2020   (JP) .................. 2020-014823

(51) Int. Cl.
*G16H 30/40*   (2018.01)
*G06T 7/00*   (2017.01)
(Continued)

(52) U.S. Cl.
CPC .......... *G16H 30/40* (2018.01); *G06T 7/0012* (2013.01); *G06V 40/10* (2022.01); *G16H 50/20* (2018.01);
(Continued)

(58) Field of Classification Search
CPC ........ G16H 30/40; G16H 50/20; G06V 40/10; G06T 7/0012; G06T 2207/10016;
(Continued)

(56) References Cited

U.S. PATENT DOCUMENTS

| 10,368,817 B2 | 8/2019 | Kreeger et al. |
| 2014/0101080 A1* | 4/2014 | Lee .................. G16H 30/40 706/12 |

(Continued)

FOREIGN PATENT DOCUMENTS

JP   201937692 A   3/2019

OTHER PUBLICATIONS

Tanaka et al., "Computer-aided diagnosis system for breast ultrasound images using deep learning"; Physics in Medicine & Biology; 2019; vol. 64, pp. 1-12.

(Continued)

*Primary Examiner* — William D Titcomb
(74) *Attorney, Agent, or Firm* — Maier & Maier, PLLC

(57) ABSTRACT

A storage medium, a diagnosis support apparatus and a diagnosis support method that enable presenting a recognition result suitable to a status of use of a CAD (computer-assisted diagnosis/detection) function are provided. A diagnosis support apparatus performs recognition processing of a breast image showing a projection image or a section image of a breast of a subject, using one or more recognizers from among a plurality of recognizers each including a neural network, and selects a recognizer to be used for the recognition processing or a recognizer that is to output a recognition result of the recognition processing, from among the plurality of recognizers, according to examination information relating to an examination of the subject.

20 Claims, 15 Drawing Sheets

(51) Int. Cl.
  *G06V 40/10* (2022.01)
  *G16H 50/20* (2018.01)
(52) U.S. Cl.
  CPC .............. *G06T 2207/10016* (2013.01); *G06T 2207/20081* (2013.01); *G06T 2207/20084* (2013.01); *G06T 2207/30068* (2013.01); *G06T 2207/30096* (2013.01)
(58) Field of Classification Search
  CPC . G06T 2207/20081; G06T 2207/20084; G06T 2207/30068; G06T 2207/30096
  USPC .......................................................... 382/128
  See application file for complete search history.

(56) References Cited

U.S. PATENT DOCUMENTS

| | | | | |
|---|---|---|---|---|
| 2015/0173705 A1* | 6/2015 | Lee | ........................ | A61B 5/055 600/407 |
| 2018/0157800 A1* | 6/2018 | Ravishankar | .......... | G16H 50/50 |
| 2018/0301222 A1* | 10/2018 | Dew, Sr. | ................. | G16H 50/20 |
| 2020/0273581 A1* | 8/2020 | Wolf | ........................ | G16H 40/63 |
| 2020/0395111 A1* | 12/2020 | Forzoni | ............... | G10L 15/1815 |
| 2023/0213601 A1* | 7/2023 | Madera | ................... | G16H 10/20 702/19 |

OTHER PUBLICATIONS

Office Action issued on Aug. 25, 2020, in connection with corresponding Japanese Application No. 2020-014823 (6 pp., including machine-generated English translation).

International Search Report (with English Translation) and Written Opinion (with Machine Translation) issued on Mar. 30, 2021 in corresponding International Patent Application No. PCT/JP2021/002960; 16 pages.

Office Action issued on Feb. 27, 2025, in corresponding Indian Application No. 202217046023, 7 pages.

* cited by examiner

FIG.7B

| ITEM | CONDITION | RECOGNIZER TYPE |
|---|---|---|
| EXAMINATION TYPE | SCREENING EXAMINATION | OUTPUT "BI-RADS" |
| | THOROUGH EXAMINATION | OUTPUT "BENIGN/ MALIGNANT" |
| DISPLAY MEANS | LOW PERFORMANCE | OUTPUT "BI-RADS" |
| | HIGH PERFORMANCE | OUTPUT "BENIGN/ MALIGNANT" |
| ... | ... | ... |

*FIG.8B*

| ITEM | CONDITION | RECOGNIZER TYPE |
|---|---|---|
| EXAMINATION TYPE PROFICIENCY OF DOCTOR | THOROUGH EXAMINATION | "SENSITIVITY" RELATIVELY HIGH |
| | SCREENING EXAMINATION AND PROFICIENCY LOW | "SPECIFICITY" RELATIVELY HIGH |
| | SCREENING EXAMINATION AND PROFICIENCY HIGH | INTERMEDIATE IN RECOGNITION PERFORMANCE BETWEEN ABOVE TWO TYPES |
| ... | ... | ... |

FIG.9B

| ITEM | CONDITION | RECOGNIZER TYPE |
|---|---|---|
| REGION | REGION A | LEARNED USING DATA ON "REGION A" |
| | REGION B | LEARNED USING DATA ON "REGION B" |
| ... | ... | ... |

*FIG.10B*

| ITEM | CONDITION | RECOGNIZER TYPE |
|---|---|---|
| DIAGNOSIS IMAGE TYPE | STILL IMAGE | ARITHMETIC OPERATION TIME RELATIVELY LONG |
| | MOVING IMAGE | ARITHMETIC OPERATION TIME RELATIVELY SHORT |
| ... | ... | ... |

STORAGE MEDIUM, DIAGNOSIS SUPPORT APPARATUS AND DIAGNOSIS SUPPORT METHOD

TECHNICAL FIELD

The present invention relates to a storage medium, a diagnosis support apparatus and a diagnosis support method.

BACKGROUND ART

Conventionally, in the medical field, techniques relating to computer-assisted diagnosis/detection (hereinafter, CAD) have been known.

Patent Literature 1 discloses an apparatus that determines whether or not a certain lesion is present within a determination range of a breast image, using a neural network machine-learned via deep learning.

CITATION LIST

Patent Literature

Patent Literature 1: Japanese Patent Laid-Open No. 2019-037692

SUMMARY OF INVENTION

Technical Problem

A neural network is built by combining various network structures and a huge number of learning parameters, and thus, can function as an image recognizer provided with a wide variety of properties. Therefore, as with the apparatus disclosed in Patent Literature 1, where recognition processing is performed consistently using a uniform neural network, the apparatus may fail to exert sufficient performance (in, for example, recognition accuracy and/or processing speed), depending on the status of use of a CAD function.

The present invention has been made in view of the aforementioned problem and an object of the present invention is to provide a storage medium, a diagnosis support apparatus and a diagnosis support method that enable presenting a recognition result suitable to a status of use of a CAD function.

Solution to Problem

A storage medium in a first aspect of the present invention stores a diagnosis support program for making one computer or a plurality of computers function as: recognition means for performing recognition processing of a breast image showing a projection image or a section image of a breast of a subject, using one or more recognizers from among a plurality of recognizers each including a neural network; and selection means for selecting a recognizer to be used for the recognition processing or a recognizer that is to output a recognition result of the recognition processing, from among the plurality of recognizers, according to examination information relating to an examination of the subject.

Also, the plurality of recognizers may include a first recognizer that outputs a value indicating a category of a lesion site and a second recognizer that outputs a value indicating a characteristic of a lesion site, and the selection means may select the first recognizer if an examination type identified by the examination information is a screening examination, and select the second recognizer if the examination type is a thorough examination.

Also, the plurality of recognizer may include a first recognizer that outputs a value indicating a category of a lesion site and a second recognizer that outputs a value indicating a characteristic of a lesion site, and the selection means may select the first recognizer if display performance of display means identified by the examination information, the display means displaying the breast image, is relatively low, and select the second recognizer if the display performance of the display means is relatively high.

Also, the first recognizer may output a value for distinguishing between BI-RADS categories, and the second recognizer may output a value for distinguishing between benignity and malignancy.

Also, the plurality of recognizers may include a first recognizer and a second recognizer having a relatively high sensitivity or a relatively low specificity in comparison with the first recognizer, and the selection means may select the first recognizer if an examination type identified by the examination information is a screening examination, and select the second recognizer if the examination type is a thorough examination.

Also, the plurality of recognizers may include a first recognizer and a second recognizer having a relatively high sensitivity or a relatively low specificity in comparison with the first recognizer, and the selection means may select the first recognizer if interpretation proficiency of a doctor or a laboratory technician (hereinafter, also simply referred to as "doctor or the like"), the interpretation proficiency being identified by the examination information, is relatively low, and select the second recognizer if the interpretation proficiency is relatively high.

Also, the plurality of recognizers may include two or more recognizers machine-learned using two or more general populations including test images collected on a region-by-region basis, and the selection means may select a recognizer corresponding to an examination conduction region identified by the examination information.

Also, the plurality of recognizers may include a first recognizer and a second recognizer whose arithmetic operation amount or arithmetic operation time of the recognition processing is relatively small or short in comparison with the first recognizer, and the selection means may select the first recognizer if a type of the breast image, the type being identified by the examination information, is a still image, and select the second recognizer if the type of the breast image is a moving image.

Also, the diagnosis support program may make the one computer or the plurality of computers further function as display control means for performing control to display recognizer information indicating a type or a property of the recognizer selected by the selection means, on display mean, together with result information indicating the recognition result.

A diagnosis support apparatus in a second aspect of the present invention includes: recognition means for performing recognition processing of a breast image showing a projection image or a section image of a breast of a subject, using a plurality of recognizers each including a neural network; and selection means for selecting a recognizer to be used for the recognition processing or a recognizer that is to output a recognition result of the recognition processing, from among the plurality of recognizers, according to examination information relating to an examination of the subject.

A diagnosis support method in a third aspect of the present invention includes making one computer or a plurality of computers execute: a recognition step of performing recognition processing of a breast image showing a projection image or a section image of a breast of a subject, using a plurality of recognizers each including a neural network; and a selection step of selecting a recognizer to be used for the recognition processing or a recognizer that is to output a recognition result of the recognition processing, from among the plurality of recognizers, according to examination information relating to an examination of the subject.

Advantageous Effect of Invention

The present invention enables presenting a recognition result suitable to a state of use of a CAD function.

BRIEF DESCRIPTION OF DRAWINGS

FIG. 7B is a diagram illustrating a first example of a selection table in which recognizer selection rules are described.

FIG. 8B is a diagram illustrating a second example of the selection table in which recognizer selection rules are described.

FIG. 9B is a diagram illustrating a third example of the selection table in which recognizer selection rules are described.

FIG. 10B is a diagram illustrating a fourth example of the selection table in which recognizer selection rules are described.

DESCRIPTION OF EMBODIMENTS

A diagnosis support program in the present invention will be described with reference to the accompanying drawings, taking an embodiment that is preferable in relation to a diagnosis support apparatus and a diagnosis support method. For ease of understanding of the description, in the respective drawings, same components and steps are provided with same signs to the extent possible and overlapping description may be omitted. Also, the term "means" may be replaced with another expression, for example, "section", "unit" or "function".

[Configuration of Medical Diagnostic Imaging System 10]

<Overall Configuration>

Figure 1:
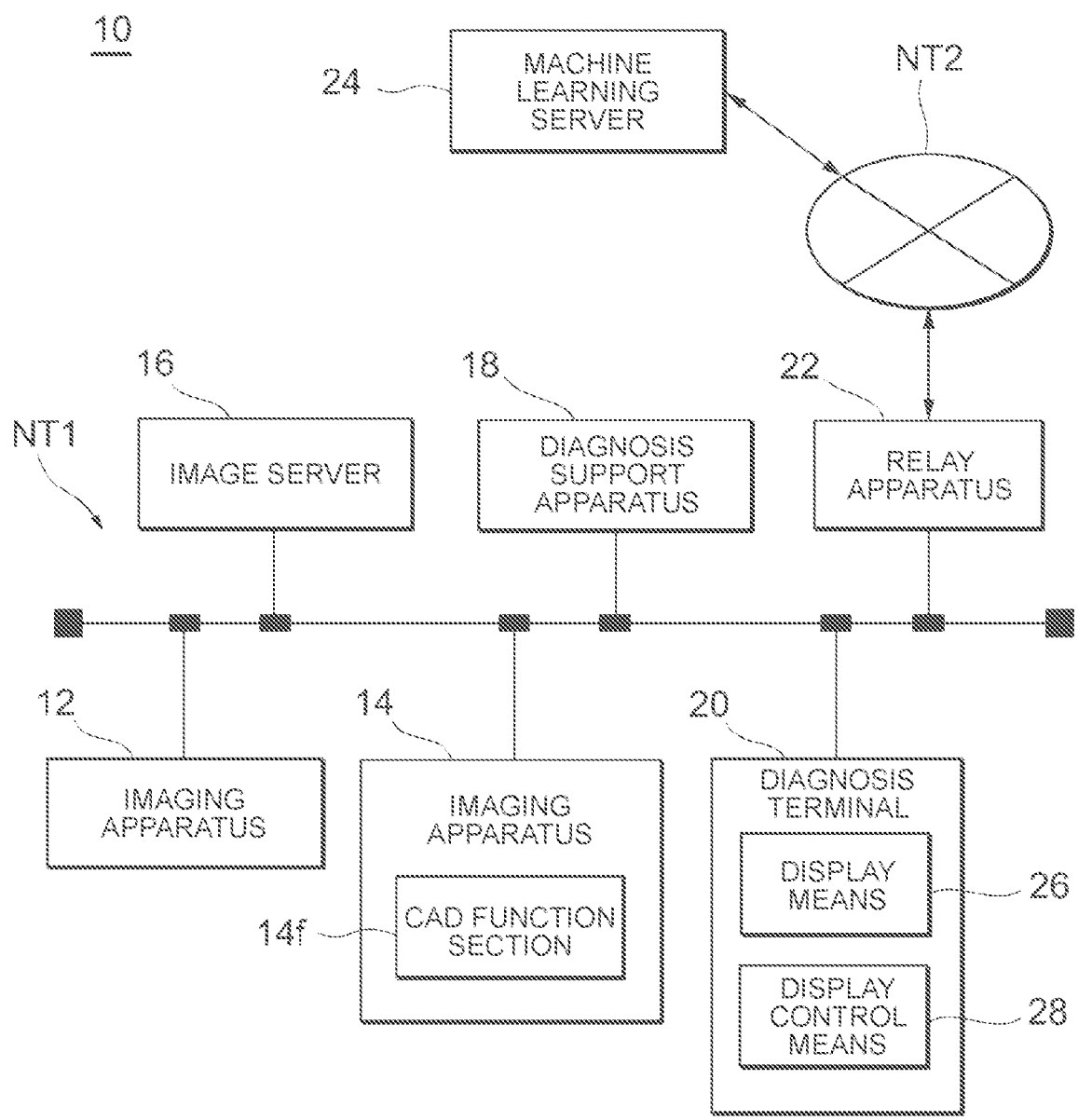
FIG. 1 is an overall configuration diagram of a medical diagnostic imaging system in an embodiment of the present invention.

FIG. 1 is an overall configuration diagram of a medical diagnostic imaging system 10 in which a diagnosis support apparatus 18 in an embodiment of the present invention is incorporated. The medical diagnostic imaging system 10 is capable of providing a computer-assisted diagnosis/detection function (that is, a CAD function) to a doctor or the like who performs medical practice in a medical facility.

The medical diagnostic imaging system 10 includes imaging apparatuses 12, 14, an image server 16, a diagnosis support apparatus 18, a diagnosis terminal 20, a relay apparatus 22 and a machine learning server 24. The respective apparatuses, etc., except the machine learning server 24 are capable of communicating with one another via an internal network NT1.

Each of the imaging apparatuses 12, 14 is an apparatus that shoots a breast image 54 (FIG. 3) showing a projected image or a section image of a breast of a subject. A type of mode of imaging (what is called "modality") may be, for example, any of ultrasound, simple X-ray, X-ray CT (computed tomography), MRI (magnetic resonance imaging), tomosynthesis and optical CT. In the case of the imaging apparatus 12 including no CAD function section, an on-demand CAD function is provided by cooperation of the image server 16, the diagnosis support apparatus 18 and the diagnosis terminal 20. On the other hand, in the case of the imaging apparatus 14 including a CAD function section 14f, a real-time CAD function is provided by operation of the imaging apparatus 14 alone.

The image server 16 is a file server that manages each of the breast images 54 acquired by the imaging apparatuses 12, 14, in association with examination information 56 and result information 58, each of which will be described later. The diagnosis support apparatus 18 is a data processing server that performs various types of recognition processing for a breast image 54 to generate various types of information for assisting a doctor or the like in making diagnosis. The diagnosis terminal 20 is a terminal apparatus for a doctor or the like to perform interpretation, and includes display means 26 including a display device, and display control means 28 for performing display control for the display means 26. The machine learning server 24 is a data processing server capable of mutually communicating with the diagnosis support apparatus 18 and the imaging apparatus 14 via an external network NT2 and the relay apparatus 22.

<Hardware Configuration of Diagnosis Support Apparatus 18>

Figure 2:
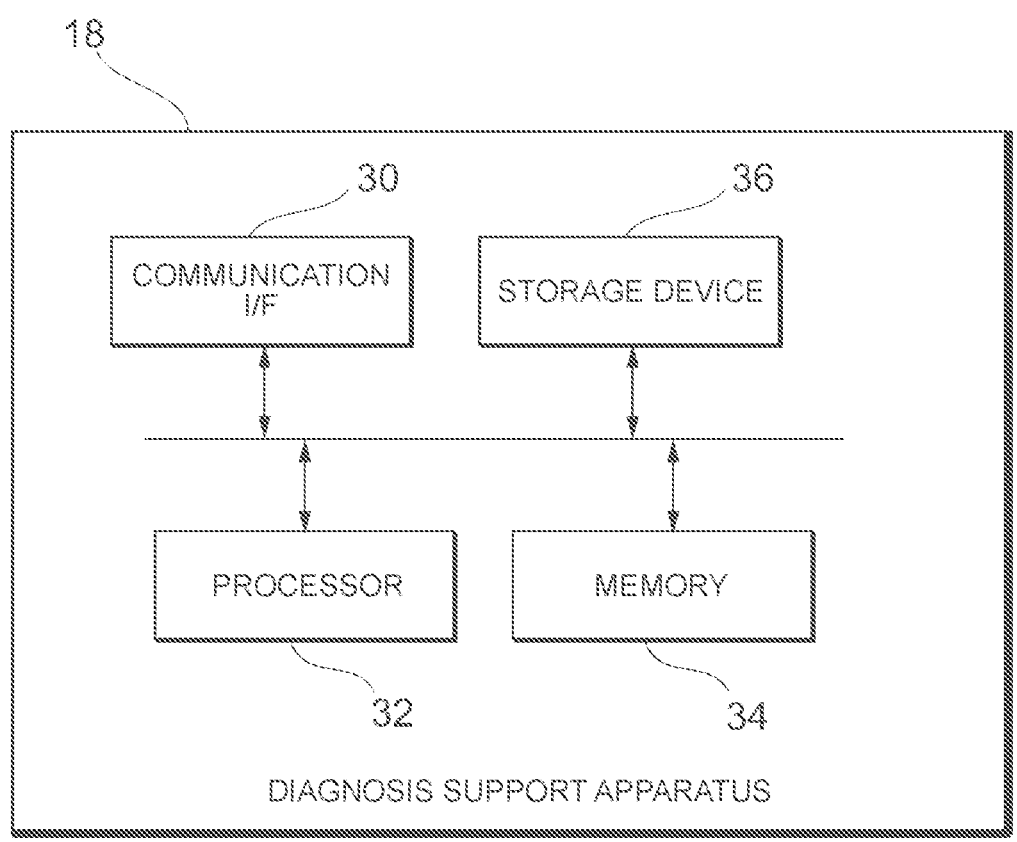
FIG. 2 is a diagram illustrating an example of a hardware configuration of a diagnosis support apparatus in FIG. 1.

FIG. 2 is a diagram illustrating an example of a hardware configuration of the diagnosis support apparatus 18 in FIG. 1. The diagnosis support apparatus 18 includes a communication I/F 30, a processor 32, a memory 34 and a storage device 36.

The communication I/F 30 is an interface that transmits and receives an electrical signal to/from an external apparatus. Consequently, the diagnosis support apparatus 18 is, for example, capable of receiving a breast image 54 (FIG. 3), which is a target of recognition processing, from the image server 16 and transmitting result information 58 (FIG. 3) indicating a result of recognition of the breast image 54 to the image server 16.

The processor 32 may be a general-purpose processor including a CPU (central processing unit) or may be a dedicated processor including a GPU (graphics processing unit) or an FPGA (field-programmable gate array). The memory 34 is a computer-readable non-transitory storage medium and stores programs and data that are necessary for the processor 32 to control the respective components. Examples of the storage device 36 include non-transitory storage mediums including a hard disk drive (HDD) and a solid-state drive (SSD).

<Functional Blocks of Diagnosis Support Apparatus 18>

Figure 3:
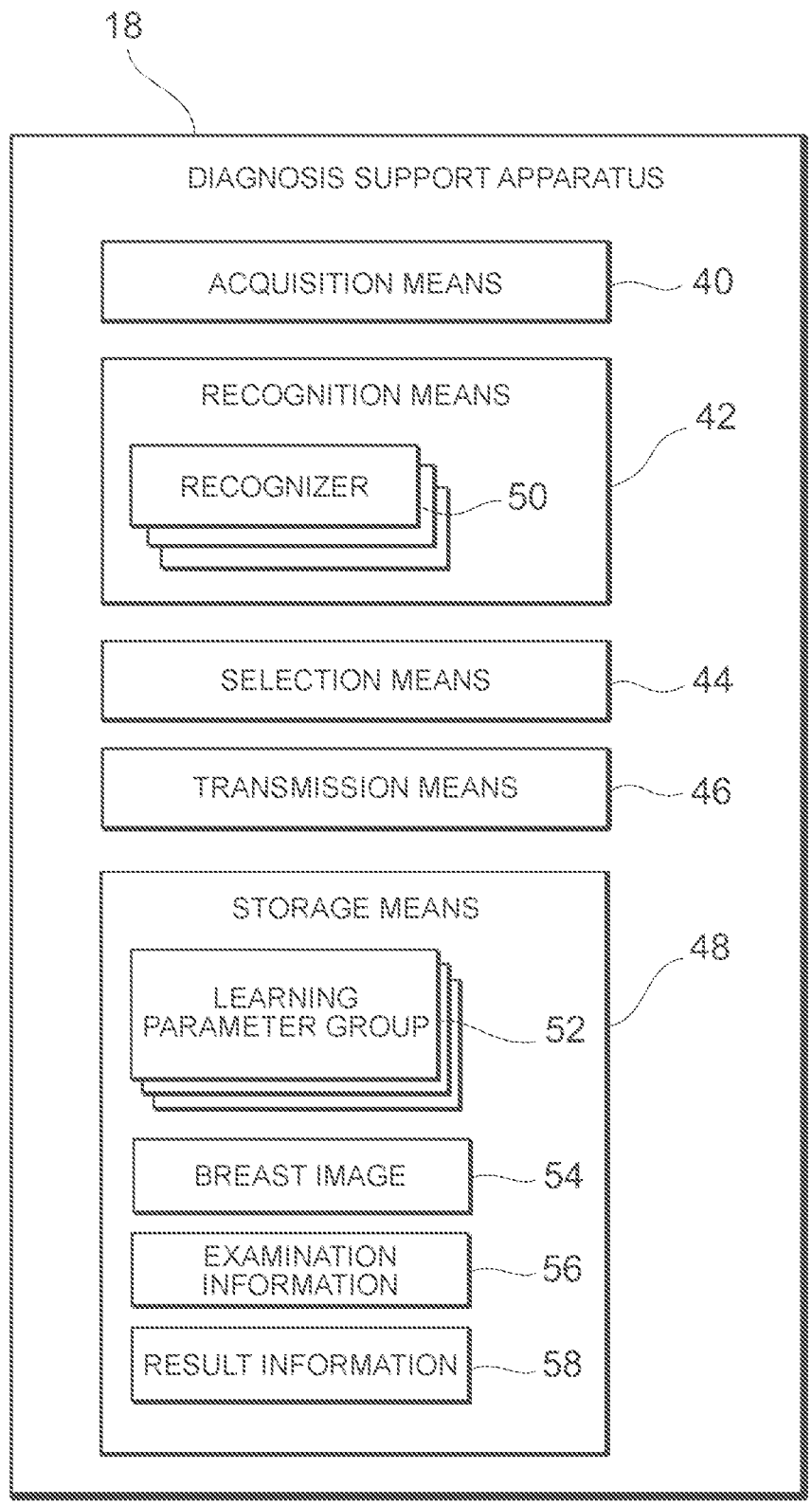
FIG. 3 is a diagram illustrating example functional blocks of the diagnosis support apparatus in FIGS. 1 and 2.

FIG. 3 is a diagram illustrating example functional blocks of the diagnosis support apparatus 18 in FIGS. 1 and 2. The diagnosis support apparatus 18 functions as acquisition means 40, recognition means 42, selection means 44, transmission means 46 and storage means 48 by a diagnosis support program stored on the memory 34 being read and executed. The acquisition means 40 is means implemented by the communication I/F 30 and the processor 32 in FIG. 2. Each of the recognition means 42 and the selection means 44 is means implemented by the processor 32 in FIG. 2. The transmission means 46 is means implemented by the communication I/F 30 and the processor 32 in FIG. 2. The storage means 48 is means implemented by the storage device 36 in FIG. 2.

The acquisition means 40 acquires a breast image 54, which is a target of recognition processing, and examination information 56 through communication with the image server 16. The acquisition means 40 may acquire examination information 56 stored in an apparatus other than the image server 16 (for example, an internal server that manages various pieces of information relating to subjects, healthcare workers or medical apparatuses). Also, the acquisition means 40 acquires one or more learning parameter groups 52 through communication with the machine learning server 24.

The recognition means 42 subjects the breast image 54 acquired by the acquisition means 40 to various types of recognition processing to output a result of recognition of the breast image 54. Also, the recognition means 42 functions as a plurality of recognizers 50 by a plurality of learning parameter groups 52 being set. The plurality of recognizers 50 include, for example, two or more recognizers that are different in at least any of output value definition, recognition performance, region of collection of test images 71 (FIG. 5) and arithmetic operation amount or arithmetic operation time.

The selection means 44 selects one recognizer 50 to be used for recognition processing, from among the plurality of recognizers 50, according to the examination information 56 associated with the breast image 54. Alternatively, the selection means 44 selects one recognizer 50 that is to output a recognition result of recognition processing, from among the plurality of recognizers 50, according to the above examination information 56.

The transmission means 46 transmits result information 58 output from the recognition means 42 to the outside. If the breast image 54 is received together with a management ID from the image server 16, the transmission means 46 transmits the result information 58 provided with the management ID to the image server 16.

The storage means 48 stores the plurality of learning parameter groups 52, the breast image 54, the examination information 56 and the result information 58. Each of the learning parameter groups 52 is an aggregate of learning parameters for determining arithmetic operation rules for a recognizer 50. The breast image 54 includes one image or a plurality of images and may be a still image or a moving image. The examination information 56 is information relating to an examination of a subject, and includes, for example, an examination ID, physical information (for example, age, gender, height, weight, etc.) of the subject, a type of the examination, a type of the display means 26, interpretation proficiency of a doctor or the like, a region of conduction of the examination and a type of the breast image 54. The result information 58 is information indicating a result of recognition by the recognition means 42, and includes, for example, existence or non-existence, the number, a type (for example, a tumor), a location, a characteristic or an accuracy of a lesion site.

<Flow of Processing in Recognizer 50>

Figure 4:
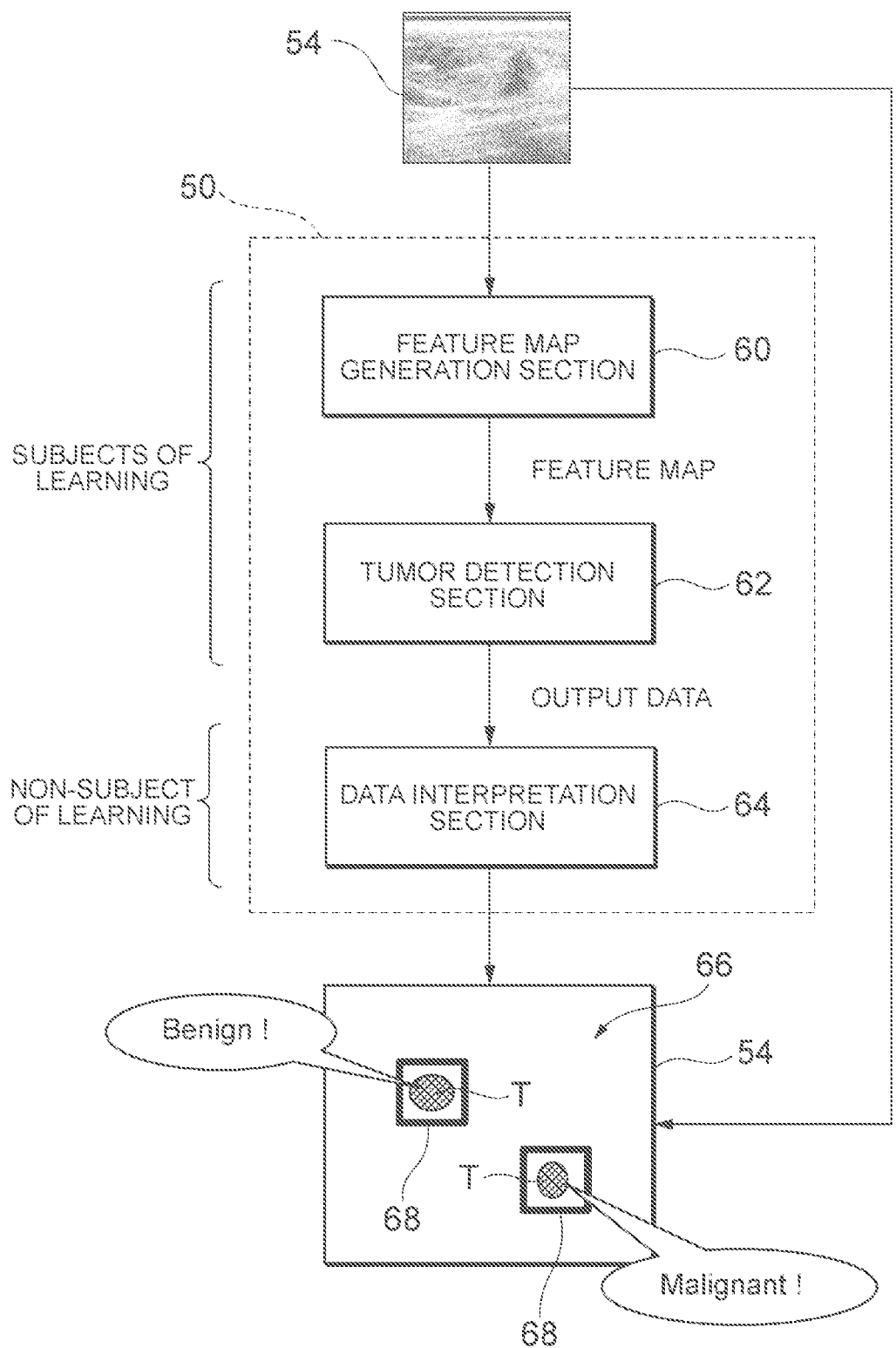
FIG. 4 is a diagram illustrating an example of a flow of processing in a recognizer in FIG. 3.

FIG. 4 is a diagram illustrating an example of a flow of processing in a recognizer 50 in FIG. 3. The recognizer 50 includes a neural network. The recognizer 50 may be configured by a neural network alone. This neural network is capable of building an "object detection model" that detects an object in an image, through machine learning (hereinafter also simply referred to as "learning"). A type of the object detection model may be a "two-stage detector" (for example, a Faster R-CNN or a model derived therefrom) in which an extractor for a region of interest (ROI) is provided separately from an object detector or a "one-stage detector" in which an extractor and a detector are configured integrally (for example, YOLO, SSD, M2Det or a model derived therefrom).

The recognizer 50 includes a feature map generation section 60, a tumor detection section 62 and a data interpretation section 64 in the order mentioned from the upstream side to the downstream side. In the example in the figure, the feature map generation section 60 and the tumor detection section 62 are subject to learning processing and the data interpretation section 64 is not subject to learning processing.

The feature map generation section 60 repeatedly executes a convolution operation and a pooling operation (what is called CNN operations) of a breast image 54 to generate a feature map indicating morphological features of the breast image 54, for each channel. The above CNN operations can be executed by various network structures including VGG16 and ResNet.

The tumor detection section 62 detects existence/non-existence and a position of a tumor area T in an entire area 66 of the breast image 54, using the feature maps for the respective channels. For example, in the case of a "YOLO" model, tensor-form output data indicating accuracies for respective classes (or probabilities with a total sum of label values normalized as 1) can be obtained as a detection result.

The data interpretation section 64 interprets the output data from the tumor detection section 62 to acquire a result of recognition of the breast image 54 (for example, existence/non-existence, the position or a characteristic of the tumor area T). Here, the position of the tumor area T may be a representative position (for example, a center of gravity) of the tumor area T or may be a position relating to a rectangular region of interest 68 that is externally tangent to the tumor area T.

<Configuration of Machine Learning Server 24>

Figure 5:
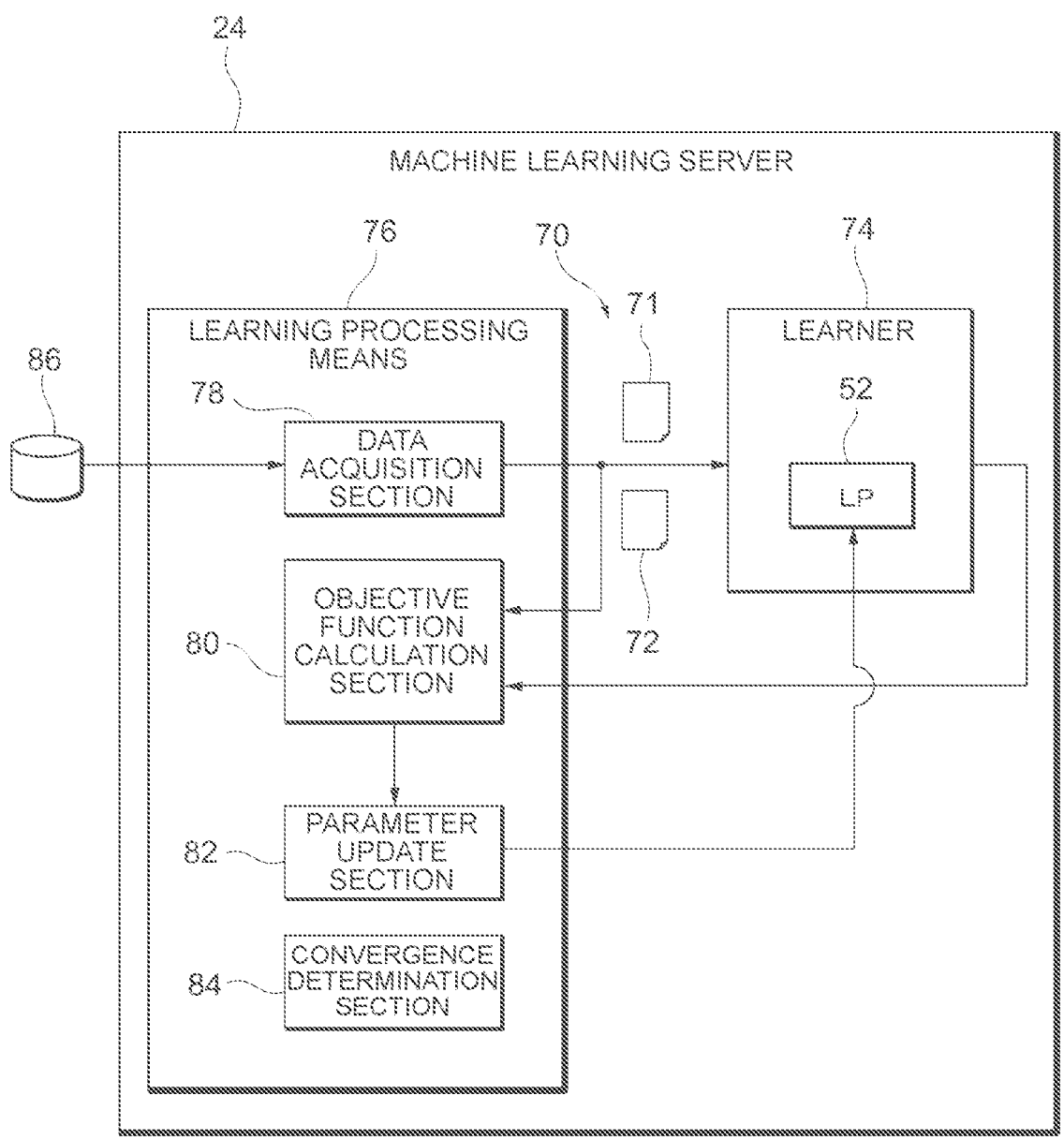
FIG. 5 is a diagram illustrating example functional blocks of a machine learning server in FIG. 1.

FIG. 5 is a functional block diagram relating to learning processing in the machine learning server 24. The machine learning server 24 performs learning processing for a learner 74, using training data 70 prepared in advance, to generate one or more learning parameter groups 52. In the figure, the learner 74 and learning processing means 76 are schematically illustrated in a configuration of the machine learning server 24.

Arithmetic operation rules for the learner 74 are determined by respective values of learning parameters forming a learning parameter group 52. The learning parameter group 52 is configured by, for example, "variable parameters" including a coefficient describing an activating function for an arithmetic operation unit and a degree of binding between arithmetic operation units, and "fixed parameters" for specifying a network structure (what is called, hyperparameters). Examples of the hyperparameters can include the number of arithmetic operation units included in each layer, the number of intermediate layers and a type of an object detection model.

The learning processing means 76 performs learning processing for the learner 74 (that is, optimization processing for the learning parameter group 52), using a plurality of sets of training data 70. The learning processing means 76 includes a data acquisition section 78, an objective function calculation section 80, a parameter update section 82 and a convergence determination section 84.

The data acquisition section 78 acquires one set or a plurality of sets of training data 70 from a database 86 prepared in advance. The training data 70 include a data set of a test image 71 and correct answer information 72. The test image 71 may be a clinical image or a phantom image or may be a pseudo image generated using a generation model including a GAN (generative adversarial network). The correct answer information 72 includes label values and position information of bounding boxes.

The objective function calculation section 80 calculates an objective function including an error between information on an output of the learner 74 for the test image 71 of the training data 70 and the correct answer information 72 for the training data 70 (hereinafter referred to as "learning error"). This learning error may be an L1 norm function that returns an absolute value of a difference or may be an L2 norm function that returns a square value of a difference. Also, this learning error may be an error in one set of training data 70 (in the case of on-line learning) or may be an error relating to a plurality of sets of training data 70 (in the case of batch learning or mini-batch learning).

The parameter update section 82 updates the learning parameter group 52 (aforementioned variable parameters) in such a manner that the objective function calculated by the objective function calculation section 80 becomes small. For an update algorithm, for example, any of various methods including a gradient descent method, a stochastic gradient descent method, a momentum method and RMSprop may be used.

The convergence determination section 84 determines whether or not a predetermined convergence condition is met at the current point of time of learning. Examples of the convergence condition can include: [1] The objective function has become sufficiently small, [2] An amount of update of the objective function has become sufficiently small and [3] The number of repetitions of learning has reached an upper limit value.

[Operation of Medical Diagnostic Imaging System 10]

The medical diagnostic imaging system 10 in which the diagnosis support apparatus 18 in an embodiment of the present invention is incorporated is configured as above. Next, overall operation of the medical diagnostic imaging system 10 and operation for selection of a recognizer 50 by the diagnosis support apparatus 18 will be descried with reference to FIGS. 1 to 3 and 6 and FIGS. 7A to 10B, respectively.

<Overall Operation>

(1. Downloading of Learning Parameter Groups 52)

The machine learning server 24 generates learning parameter groups 52 through new learning or additional learning. Then, in response to a request from the diagnosis support apparatus 18 or the imaging apparatus 14, the machine learning server 24 transmits the learning parameter groups 52 stored in the machine learning server to the source of the request. Consequently, the diagnosis support apparatus 18 or the imaging apparatus 14 becomes able to use latest-version recognizers 50 by acquiring and storing the learning parameter groups 52 from the machine learning server 24.

(2. Shooting Image of Subject)

A doctor or the like performs work for shooting an image of a breast of a subject, using the imaging apparatus 12. After the image shooting, the imaging apparatus 12 transmits a breast image 54 generated by the imaging apparatus to the image server 16, with the breast image 54 linked with a subject ID and examination information 56. Consequently, a data set (hereinafter, "diagnosis information") including the breast image 54 and the examination information 56 is stored in the image server 16. Note that no result information 58 is included in the diagnosis information of the current point of time.

(3. Recognition Processing)

The diagnosis support apparatus 18 regularly or irregularly inquires the image server 16 about whether or not there is an unprocessed breast image 54. If there is an unprocessed breast image 54, the acquisition means 40 of the diagnosis support apparatus 18 acquires relevant diagnosis information and a management ID thereof from the image server 16.

The selection means 44 selects one recognizer 50 to be used for recognition processing, from among the plurality of recognizers 50 available for the recognition means 42, according to whether or not the examination information 56 included in the diagnosis information meets a predetermined condition. For example, the selected recognizer 50 can be used by the selection means 44 reading a relevant learning parameter group 52 from the storage means 48 and supplying the learning parameter group 52 to the recognition means 42.

The recognition means 42 performs recognition processing of the breast image 54, using the selected recognizer 50 to output result information 58 indicating a result of recognition of the breast image 54. The transmission means 46 transmits the obtained result information 58 to the image server 16, with the result information 58 linked to the management ID.

Consequently, the diagnosis information including the breast image 54, the examination information 56 and the result information 58 is stored in the image server 16.

(4. Display of Diagnosis Screen 100)

A doctor or the like performs an operation to request display of a diagnosis screen 100 (FIG. 6) of a subject to be diagnosed, using the diagnosis terminal 20. Then, the diagnosis terminal 20 transmits a signal to request diagnosis information for the designated subject (that is, a request signal) to the image server 16. In response to the request signal from the diagnosis terminal 20, the image server 16 transmits diagnosis information including a breast image 54, examination information 56 and result information 58 (FIG. 3) to the diagnosis terminal 20.

Upon reception of the diagnosis information from the image server 16, the display control means 28 of the diagnosis terminal 20 generates display data for the diagnosis screen 100 using the diagnosis information and then supplies the display data to the display means 26. Consequently, the diagnosis screen 100 in FIG. 6 is displayed in a non-illustrated display area of the display means 26.

Figure 6:
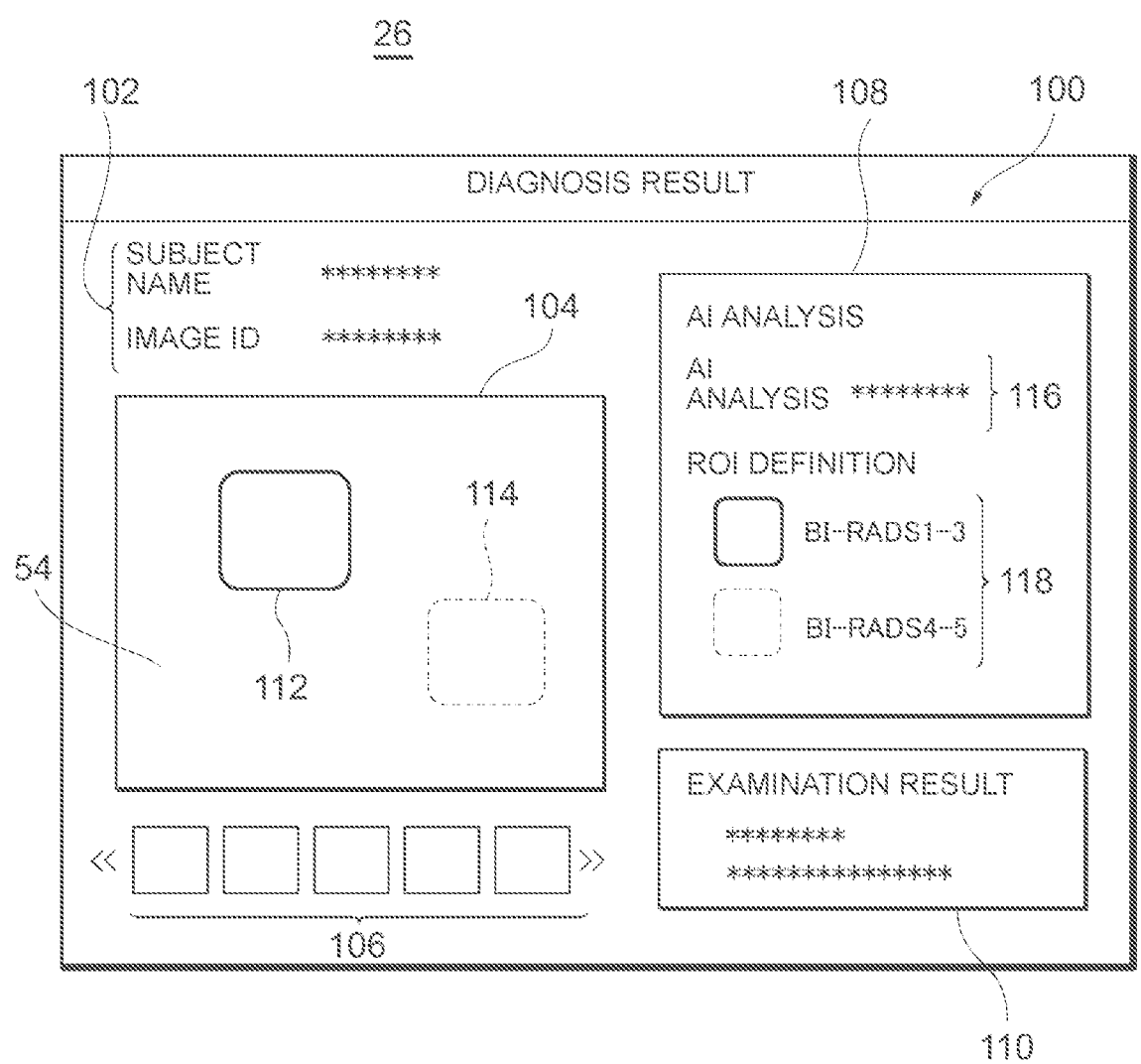
FIG. 6 is a diagram illustrating an example of a diagnosis screen for a subject.

As illustrated in FIG. 6, an examination information section 102, an image section 104, a thumbnail section 106, a processing information section 108 and an examination result section 110 are provided in the diagnosis screen 100. In the examination information section 102, the examination information 56 including a subject name and an image ID is displayed. In the image section 104, one designated breast image 54 is displayed. On the breast image 54, each of marks 112, 114 each indicating a rounded rectangular frame is displayed in a superimposed manner at a position at which the mark surrounds a tumor. The thumbnail section 106 is configured to enable selecting one to be displayed in the image section 104 from among a plurality of breast images 54, through a UI (user interface).

In the processing information section 108, recognizer information 116 representing a type or a property of a recognizer 50 and explanatory information 118 for explaining respective meanings of the marks 112, 114 are displayed. The recognizer information 116 includes, for example, a name of the recognizer 50, a name of an object detection model, a feature of recognition property (for example, a high sensitivity type, a high specificity type or a balanced type) and a suggested user name (for example, for beginners or for experts).

Note that the result information 58 is displayed in such a manner that the doctor or the like can grasp a result of recognition by the recognition means 42 at first view. In the example in the figure, the result information 58 is visualized as the marks 112, 114 in the image section 104 and the descriptive information 118 in the processing information section 108. Also, since the recognizer information 116 is displayed together with the result information 58, the doctor or the like can grasp the displayed recognition result in association with the type or the property of the recognizer 50.

Here, the doctor or the like performs interpretation of the breast image 54 while viewing the image section 104 and the processing information section 108 on the diagnosis screen 100, and inputs findings and comments relating to the examination result into the examination result section 110. In this way, the diagnosis support operation by the medical diagnostic imaging system 10 ends.

In the example operation above, the recognition means 42 performs recognition processing using the recognizer 50 selected by the selection means 44, alone; however, instead, the recognition means 42 may perform a plurality of types of recognition processing for a same breast image 54 to obtain respective recognition results. In this case, the selection means 44 may select a recognizer 50 that is to output a recognition result of recognition processing, from among the plurality of recognizers 50.

<Operation for Selection of Recognizer 50>

Subsequently, an operation for selection of a recognizer 50 by the selection means 44 included in the diagnosis support apparatus 18 will be described with reference to FIGS. 7A to 10B.

FIRST EXAMPLE

Definition of Output Value

In a first example of the selection operation, it is assumed that the plurality of recognizers 50 implemented in the recognition means 42 include two or more recognizers 50 that are different in output value definition. The "output value definition" means a method for expression of a lesion site that is a detection target, and examples of the "output value definition" include a type, a characteristic and a category of a lesion site. More specifically, examples of the type include, e.g., tumor and microcalcification. Examples of the characteristic include, e.g., benignity and malignancy. Examples of the category include, e.g., categories 1 to 5 and subcategories 4A/4B/4C of BI-RADS (Breast Imaging Reporting and Data System) classification.

Figure 7A:
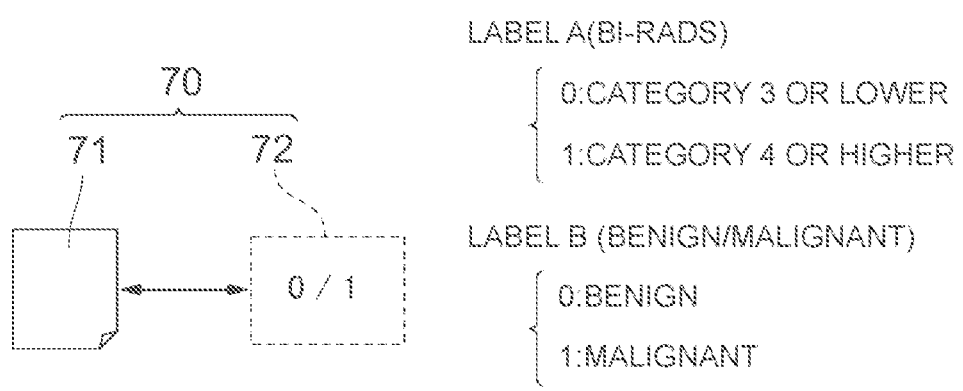
FIG. 7A is a schematic diagram illustrating a method for generating recognizers that are different in output value definition.

FIG. 7A is a schematic diagram illustrating a method for generating recognizers 50 that are different in output value definition. Here, binary labels A, B that are different in label value definition are prepared from the test image 71 and the correct answer information 72 included in the training data 70 and then learned by respective learners 74 having a same network structure. For example, for label A, a label value of "0" indicates "category 3 or lower" in BI-RADS classification and a label value of "1" indicates "category 4 or higher" in BI-RADS classification. On the other hand, for label B, a label value of "0" indicates "benign" and a label value of "1" indicates "malignant".

FIG. 7B illustrates a first example of a selection table in which rules for selection of a recognizer 50 are described. If an examination type is "screening examination", a recognizer 50 that outputs a category determination value of "BI-RADS" is selected. Consequently, at the time of a screening examination, the recognizer 50 gives support to objective determination by a doctor or the like. On the other hand, if the examination type is "thorough examination", a recognizer 50 that outputs a characteristic determination value of "benign/malignant" is selected. Consequently, at the time of a thorough examination, the recognizer 50 gives support to correct determination or decision-making by a doctor or the like.

In the case of a thorough examination, higher-performance display means 26 tends to be used in comparison with a case of a screening examination. Therefore, instead of the examination type, a type of the display means 26 may be used. For example, if the type of the display means 26 belongs to a "first group" in which display performance is relatively low, a recognizer 50 that outputs a category determination value of "BI-RADS" is selected. On the other hand, if the type of the display means 26 belongs to a "second group" in which display performance is relatively high, a recognizer 50 that outputs a characteristic determination value of "benign/malignant" is selected. Note that the classification into the first/second group may be performed in advance from various perspectives such as a model, a management state, product specifications and usage (for example, for interpretation/electronic health record) of the display means 26 or may be performed by threshold value determination using any of quantitative values including a luminance and a resolution.

SECOND EXAMPLE

Recognition Performance

In a second example of the selection operation, it is assumed that the plurality of recognizers 50 implemented in the recognition means 42 include two or more recognizers 50 that are different in recognition performance. The "recognition performance" is evaluated based on, e.g., a sensitivity, a specificity or an AUC (area under the curve) score of an ROC (receiver operating characteristic) curve.

Figure 8A:
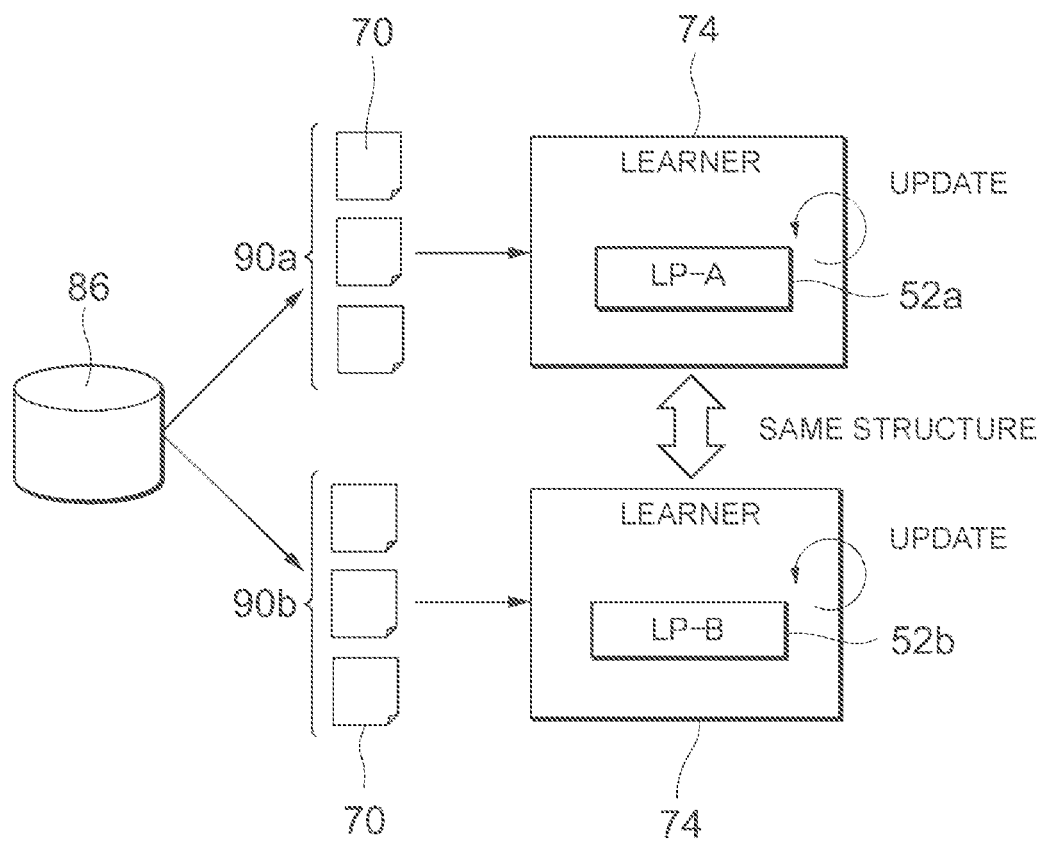
FIG. 8A is a schematic diagram illustrating a method for generating recognizers that are different in recognition performance.

FIG. 8A is a schematic diagram illustrating a method for generating recognizers 50 that are different in recognition performance. For example, different general populations A, B are formed from the database 86 in which the training data 70 is stored and then are learned by respective learners 74 having a same network structure. For example, a learning parameter group 52a is generated through learning using a training data group 90a forming general population A. On the other hand, a learning parameter group 52b is generated through learning using a training data group 90b forming general population B. Note that general populations A, B may be different in distribution of samples or number of samples or may be different in proportion of positive and negative cases or proportion of training data and verification data.

FIG. 8B illustrates a second example of the selection table in which rules for selection of a recognizer 50 are described. If an examination type is "thorough examination", a recognizer 50 that is high in "sensitivity" in comparison with a screening examination is selected. Consequently, a false-negative rate is lowered and the possibility of a subject that "is" diseased being erroneously diagnosed as "not being" diseased is lowered. On the other hand, if the examination type is "screening examination", a recognizer 50 that is high in "specificity" in comparison with a thorough examination is selected. Consequently, a false-positive rate is lowered and the possibility of a subject that "is not" diseased being erroneously diagnosed as "being" diseased is lowered.

A doctor or the like having low proficiency tends to take time for diagnosis because of unfamiliarity with interpretation. Therefore, along with or separately from the examination type, interpretation proficiency of a doctor or the like may be used. For example, if the examination type is "screening examination" and the proficiency of the doctor or the like belongs to a "first group" in which the proficiency of the doctor is relatively low, the above-described recognizer 50 that is high in "specificity" is selected. On the other hand, if the examination type is "screening examination" and the proficiency of the doctor or the like belongs to a "second group" in which the proficiency of the doctor or the like is relatively high, a recognizer 50 that is "intermediate" in recognition performance between the above two types is selected. Consequently, improper diagnosis of false-positive by a doctor or the like having low proficiency is more likely to be curbed at the time of a screening examination. Note that the classification into the first/second group may be performed in advance from various perspectives such as experience, position, qualification or age of the doctor or the like or may be performed via threshold determination using quantitative values including experience/age.

THIRD EXAMPLE

Region of Collection of Test Images 71

In a third example of the selection operation, it is assumed that the plurality of recognizers 50 implemented in the recognition means 42 include two or more recognizers 50 learned using two or more general populations including test images 71 collected at different regions. The "collection regions" means regions that are statistically significantly different in, e.g., subject size or food culture, and are classified by, for example, community of states, country, prefecture or state.

Figure 9A:
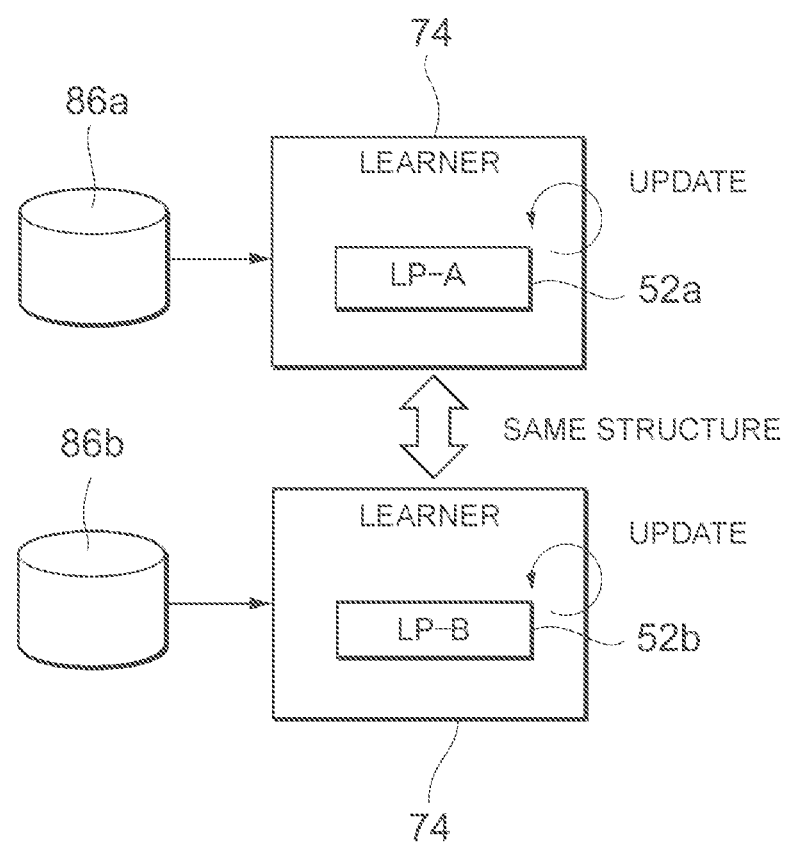
FIG. 9A is a schematic diagram illustrating a method for generating recognizers that are different in general population of training data.

FIG. 9A is a schematic diagram illustrating a method for generating recognizers 50 that are different in region of collection of test images 71. For example, databases 86a, 86b in which training data 70 including test images 71 for respective regions are accumulated are built and then are learned by respective learners 74 having a same network structure. For example, a learning parameter group 52a is generated through learning using the database 86a. On the other hand, a learning parameter group 52b is generated through learning using the database 86b.

FIG. 9B illustrates a third example of the selection table in which rules for selection of a recognizer 50 are described. If a region of conduction of an examination is "region A", a recognizer 50 for which the learning parameter group 52a for region A is set is selected. On the other hand, if the region of conduction of an examination is "region B", a recognizer 50 for which the learning parameter group 52b for region B is set is selected. Consequently, recognition processing suitable to a subject in the region of conduction can be performed and recognition accuracy is enhanced accordingly.

FOURTH EXAMPLE

Arithmetic Operation Amount/Arithmetic Operation Time

In a fourth example of the selection operation, it is assumed that a plurality of recognizers 50 implemented in the recognition means 42 include two or more recognizers 50 that are different in arithmetic operation time or arithmetic operation amount.

Figure 10A:
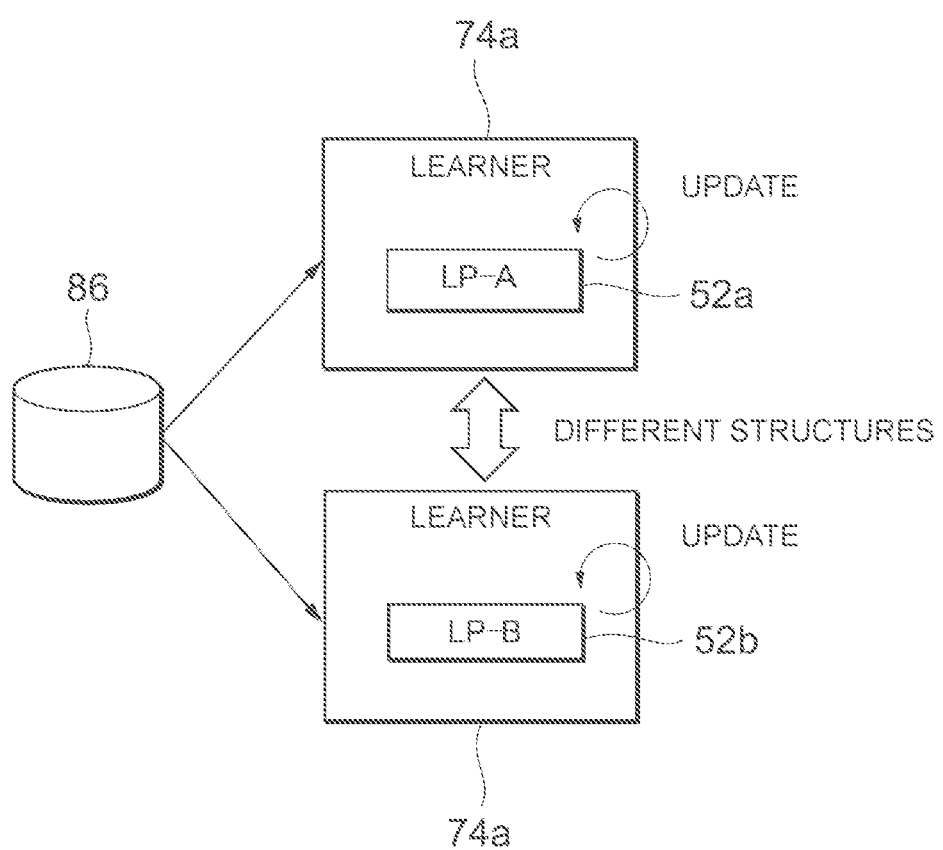
FIG. 10A is a schematic diagram illustrating a method for generating recognizers that are different in neural network structure.

FIG. 10A is a schematic diagram illustrating a method for generating recognizers 50 that are different in arithmetic operation time or arithmetic operation amount. For example, each of learners 74a, 74b having different network structures are made to learn using the training data 70 accumulated in the database 86. For example, a learning parameter group 52a is a parameter set suitable to the learner 74a and a learning parameter group 52b is a parameter set suitable to the learner 74b. Note that the learners 74a, 74b may be different in hyperparameter specifying a network structure or may be different in object detection model type.

FIG. 10B illustrates a fourth example of the selection table in which rules for selection of a recognizer 50 are described. If the type of the breast image 54 is "still image", a recognizer 50 whose arithmetic operation time is long (or whose arithmetic operation amount is large) in comparison with "moving image" is selected. On the other hand, if the type of the breast image 54 is "moving image", a recognizer 50 whose arithmetic operation time is short (or whose arithmetic operation amount is small) in comparison with "still image" is selected. Consequently, recognition processing suitable to a still image or a moving image can selectively be performed.

FIFTH EXAMPLE

The first to fourth examples may be combined as long as such combination causes no contradiction. In other words, a recognizer 50 may be selected with attention paid to two or more features of [1] output value definition, [2] recognition performance, [3] test image collection region and [4] arithmetic operation amount/arithmetic operation time.

Effects Provided by Embodiment

As above, the diagnosis support apparatus 18 includes: the recognition means 42 for performing recognition processing of a breast image 54 showing a projection image or a section image of a breast of a subject, using one or more recognizers 50 from among a plurality of recognizers 50 each including a neural network; and the selection means 44 for selecting a recognizer 50 to be used for the recognition processing or a recognizer 50 that is to output a recognition result of the recognition processing, from among the plurality of recognizers 50, according to examination information 56 relating to an examination of the subject.

Also, in the diagnosis support method and program, one computer or a plurality of computers perform recognition processing of a breast image 54 showing a projection image or a section image of a breast of a subject, using a plurality of recognizers 50 each including a neural network, and select a recognizer 50 to be used for the recognition processing or a recognizer 50 that is to output a recognition result of the recognition processing from among the plurality of recognizers 50, according to examination information 56 relating to an examination of the subject. Such configuration enables selectively outputting the recognition result of the recognition processing according to the examination of the subject and thus enables presenting a recognition result suitable to a status of use of a CAD function.

Also, where the plurality of recognizers 50 include a first recognizer that outputs a value indicating a category of a lesion site and a second recognizer that outputs a value indicating a characteristic of a lesion site, the selection means 44 may select the first recognizer if an examination type identified by the examination information 56 is a screening examination, and select the second recognizer if the examination type is a thorough examination. Consequently, at the time of a screening examination, the recognizer gives support to objective determination by a doctor or the like, and at the time of a thorough examination, the recognizer gives support to correct determination or decision-making by a doctor or the like.

Also, where the plurality of recognizers 50 includes a first recognizer that outputs a value indicating a category of a lesion site and a second recognizer that outputs a value indicating a characteristic of a lesion site, the selection means 44 may select the first recognizer if display performance of display means 26 identified by the examination information 56, the display means 26 displaying the breast image 54, is relatively low, and select the second recognizer if the display performance of the display means 26 is relatively high. Consequently, under a condition in which the probability of a screening examination being conducted is high, the recognizer gives support to objective determination by a doctor or the like, and under a condition in which in which the probability of a thorough examination being conducted is high, the recognizer gives support to correct determination or decision-making by a doctor or the like.

In this case, the first recognizer may output a value for distinguishing between BI-RADS categories, and the second recognizer may output a value for distinguishing between benignity and malignancy.

Also, where the plurality of recognizers 50 includes a first recognizer and a second recognizer having a relatively high sensitivity or a relatively low specificity in comparison with the first recognizer, the selection means 44 may select the first recognizer if the examination type identified by the examination information 56 is a screening examination and select the second recognizer if the examination type is a thorough examination. Consequently, the possibility of improper diagnosis as false-positive at the time of a screening examination is lowered and the possibility of improper diagnosis as false-negative at the time of a thorough examination is lowered.

Also, where the plurality of recognizers 50 includes a first recognizer and a second recognizer having a relatively high sensitivity or a relatively low specificity in comparison with the first recognizer, the selection means 44 may select the first recognizer if interpretation proficiency of a doctor or the like, the interpretation proficiency being identified by the examination information 56, is relatively low, and select the second recognizer if the interpretation proficiency is relatively high. Consequently, improper diagnosis of false-positive by a doctor or the like having low interpretation proficiency is more likely to be curbed at the time of a screening examination.

Also, where the plurality of recognizers 50 include two or more recognizers 50 machine-learned using general populations including test images 71 collected in different regions, the selection means 44 may select a recognizer 50 corresponding to an examination conduction region identified by the examination information 56. Consequently, recognition processing suitable to a subject in the conduction region can be performed and recognition accuracy is enhanced accordingly.

Also, where the plurality of recognizers 50 include a first recognizer and a second recognizer whose arithmetic operation amount or arithmetic operation time is relatively small or short in comparison with the first recognizer, the selection means 44 may select the first recognizer if a type of the breast image 54, the type being determined by the examination information 56, is a still image, and select the second recognizer if the type of the breast image 54 is a moving image. Consequently, recognition processing suitable to a still image or a moving image can selectively be performed.

Also, the diagnosis support apparatus 18 or the diagnosis terminal 20 may further include display control means 28 for performing control to display recognizer information 116 indicating a type or a property of the recognizer 50 selected by the selection means 44, on the display means 26, together with the result information 58 indicating the recognition result. Consequently, a doctor or the like can grasp the displayed result information 58 in association with the type or the property of the recognizer 50 by viewing the recognizer information 116.

[Alterations]

Note that the present invention is not limited to the above embodiment and it should be understood that changes can freely be made without departing from the spirit of the invention. Alternatively, the respective configurations may arbitrarily be combined as long as such combination causes no technical contradiction.

The above embodiment has been described taking a breast as an example of a shot site of a subject, but can be applied to various human body parts other than a breast. Also, the above embodiment has been described taking a tumor as an example of the lesion site, which, however, may be any of other lesions including microcalcification. In particular, where two or more lesion sites are to be detected, a recognizer 50 may output recognition results relating to a plurality of classification classes. Also, in the above embodiment, a recognizer 50 outputs a result of BI-RADS classification as a binary value; however, instead, a recognizer 50 may output any of label values for respective categories (1 to 5) or sub-categories (4A to 4C).

In the above embodiment, the selection means 44 selects one recognizer 50 from among the plurality of recognizers 50; however, instead, two or more recognizers 50 may be selected simultaneously. In this case, the display control means 28 may make obtained two or more recognition results be simultaneously displayed on the display means 26 or may make one recognition result obtained by synthesis of the two or more recognition results be displayed on the display means 26.

In the above embodiment, the selection means 44 selects a recognizer 50 using at least any of the examination type, the type of the display means 26, the interpretation proficiency, the examination conducted region and the type of the breast image 54; however, examination information 56, which is a basis for the selection, is not limited to these examples. For example, the selection means 44 may select a recognizer 50 according to an age or weight category of a subject, using physical information of the subject.

In the above embodiment, each recognizer 50 is configured of a single neural network; however, instead, each recognizer 50 may be configured of two or three or more neural networks having different functions.

Figure 11:
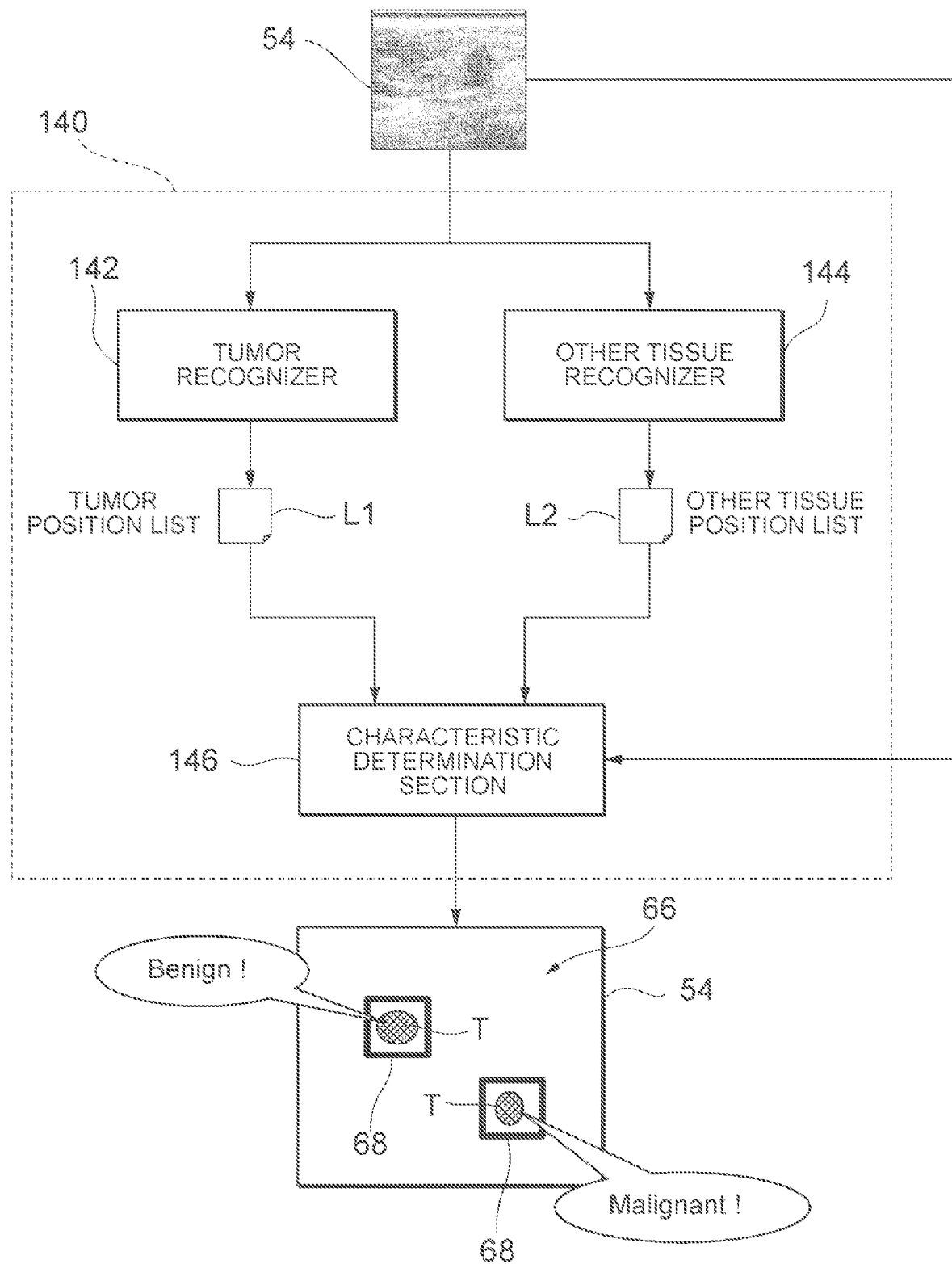
FIG. 11 is a diagram illustrating a flow of processing in a recognizer in an alteration.

FIG. 11 is a diagram illustrating a flow of processing in a recognizer 140 in an alteration. The recognizer 140 includes a tumor recognizer 142, an other tissue recognizer 144 and a characteristic determination section 146. Note that examples of "other tissue" include, e.g., a bone, a muscle, a mammary gland and fat.

The tumor recognizer 142 is a recognizer that receives an input of a breast image 54 and outputs a result of recognition of a tumor in the breast image 54. The tumor recognizer 142 includes a neural network. As the above recognition result, for example, a list including position information of a tumor area T and the probability of benignity/malignancy (hereinafter referred to as "tumor position list L1") is output.

The other tissue recognizer 144 is a recognizer that receives an input of a breast image 54 and outputs a result of recognition of another tissue in the breast image 54. The other tissue recognizer 144 includes a neural network. As the above recognition result, for example, a list including position information of the other tissue and the probability (hereinafter referred to as "other tissue position list L2") is output.

The characteristic determination section 146 identifies a positional relationship between a plurality of areas, using the tumor position list L1 and the other tissue position list L2, and based on the positional relationship, determines a characteristic of a tumor, for example, whether the tumor is benign or malignant. More specifically, if the tumor area T is located on the side away from the body surface relative to a bone area or a muscle area, the tumor area T is determined as not being a tumor. Also, if a plurality of tumor areas T do not overlap each other, each of the relevant tumors is determined as benign/malignant, using the probability output from the tumor recognizer 142 as it is. Also, if two or more tumor areas T at least partially overlap each other, a maximum value of two or more probabilities output from the tumor recognizer 142 is obtained, and the relevant tumor is determined as benign/malignant, using the maximum value of the probabilities.

REFERENCE SIGNS LIST

10 . . . medical diagnostic imaging system, 12, 14 . . . imaging apparatus, 14f . . . CAD function, 18 . . . diagnosis support apparatus, 20 . . . diagnosis terminal, 26 . . . display means, 28 . . . display control means, 34 . . . memory (storage medium), 42 . . . recognition means, 44 . . . selection means, 50, 140 . . . recognizer, 54 . . . breast image, 56 . . . examination information, 58 . . . result information, 100 . . . diagnosis screen, 112, 114 . . . mark (result information), 116 . . . recognizer information, 118 . . . explanatory information (result information)

The invention claimed is:

1. A storage medium storing a diagnosis support program for making one computer or a plurality of computers having at least one processor and at least one memory perform steps of:
retrieving examination information relating to an examination of the subject, said examination information comprising a type of examination to be performed selected from a predetermined plurality of examination types;
based on the examination information, automatically selecting a recognizer to be used for recognition processing of a breast image showing a projection image or a section image of a breast of a subject or a recognizer that is to output a recognition result of the recognition processing, from among a plurality of recognizers comprising at least a first recognizer and a second recognizer each including a neural network, wherein the first recognizer is associated with a first type of examination and the second recognizer is associated with a second type of examination, wherein the first recognizer is a recognizer trained on a first data set to have a lower false-positive rate than the second recognizer, and wherein the second recognizer is a recognizer trained on a second data set different from the first data set to have a lower false-negative rate than the first recognizer; and
with the first recognizer or the second recognizer, performing the recognition processing.

2. The storage medium according to claim 1, wherein the plurality of recognizers include a first recognizer that outputs a value indicating a category of a lesion site and a second recognizer that outputs a value indicating a characteristic of a lesion site; and
the processor selects the first recognizer if an examination type identified by the examination information is the first type of examination, and selects the second recognizer if the examination type is the second type of examination.

3. The storage medium according to claim 1, wherein the plurality of recognizers include a first recognizer that outputs a value indicating a category of a lesion site and a second recognizer that outputs a value indicating a characteristic of a lesion site; and
the processor selects the first recognizer if display performance of a display identified by the examination information, the display displaying the breast image, is lower than a threshold, and selects the second recognizer if the display performance of the display is higher than the threshold.

4. The storage medium according to claim 2, wherein the first recognizer outputs a value for distinguishing between Breast Imaging Reporting and Data System (BI-RADS) categories; and
the second recognizer outputs a value for distinguishing between benignity and malignancy.

5. The storage medium according to claim 2, wherein the plurality of recognizers include a first recognizer and a second recognizer, the second recognizer having a higher sensitivity than the first recognizer or a lower specificity than the first recognizer; and
the processor selects the first recognizer if interpretation proficiency of a doctor or a laboratory technician, the interpretation proficiency being identified by the examination information, is lower than a threshold, and selects the second recognizer if the interpretation proficiency is higher than the threshold.

6. The storage medium according to claim 1, wherein the plurality of recognizers include a first recognizer and a second recognizer, the second recognizer having a higher sensitivity than the first recognizer or a lower specificity than the first recognizer; and the processor selects the first recognizer if an examination type identified by the examination information is the first type of examination, and selects the second recognizer if the examination type is the second type of examination.

7. The storage medium according to claim 1, wherein the plurality of recognizers include two or more recognizers machine-learned using two or more general populations including test images collected on a region-by-region basis; and the processor selects a recognizer corresponding to an examination conduction region identified by the examination information.

8. The storage medium according to claim 1, wherein the plurality of recognizers include a first recognizer and a second recognizer whose arithmetic operation amount or arithmetic operation time is smaller or shorter than an amount or time of the first recognizer; and the processor selects the first recognizer if a type of the breast image, the type being identified by the examination information, is a still image, and selects the second recognizer if the type of the breast image is a moving image.

9. The storage medium according to claim 1, wherein the diagnosis support program makes the one computer or the plurality of computers further function for performing control to display recognizer information indicating a type or a property of the recognizer selected by the processor, on a display, together with result information indicating the recognition result.

10. A storage medium according to claim 1, wherein:

the first recognizer is configured to identify potential lesion sites and classify the potential lesion sites into a plurality of categories, and the second recognizer is configured to, based on an identified list of potential lesion sites, output a characteristic for one or more of the potential lesion sites in the identified list.

11. A diagnosis support apparatus comprising at least one computer having a processor and having a memory configured to cause the processor to perform steps of:

retrieving examination information relating to an examination of the subject, said examination information comprising a type of examination to be performed selected from a predetermined plurality of examination types;

based on the examination information, automatically selecting a recognizer to be used for recognition processing of a breast image showing a projection image or a section image of a breast of a subject or a recognizer that is to output a recognition result of the recognition processing, from among a plurality of recognizers comprising at least a first recognizer and a second recognizer each including a neural network, wherein the first recognizer is associated with a first type of examination and the second recognizer is associated with a second type of examination, wherein the first recognizer is a recognizer trained on a first data set to have a lower false-positive rate than the second recognizer, and wherein the second recognizer is a recognizer trained on a second data set different from the first data set to have a lower false-negative rate than the first recognizer; and with the first recognizer or the second recognizer, performing the recognition processing.

12. The support diagnosis apparatus according to claim 11, wherein the plurality of recognizers include a first recognizer that is configured to output a value indicating a category of a lesion site and a second recognizer that is configured to output a value indicating a characteristic of a lesion site; and the processor is configured to select-selects the first recognizer if an examination type identified by the examination information is the first type of examination, and selects the second recognizer if the examination type is the second type of examination.

13. The diagnosis support apparatus according to claim 11, wherein the plurality of recognizers include a first recognizer that is configured to output a value indicating a category of a lesion site and a second recognizer that is configured to output a value indicating a characteristic of a lesion site; and the processor is configured to select the first recognizer if display performance of a display identified by the examination information, the display displaying the breast image, is lower than a threshold, and is configured to select the second recognizer if the display performance of the display is higher than the threshold.

14. The diagnosis support apparatus according to claim 12, wherein the first recognizer is configured to output a value for distinguishing between Breast Imaging Reporting and Data System (BI-RADS) categories; and the second recognizer is configured to output a value for distinguishing between benignity and malignancy.

15. The diagnosis support apparatus according to claim 11, wherein the plurality of recognizers include a first recognizer and a second recognizer, the second recognizer having a higher sensitivity than the first recognizer or a lower specificity than the first recognizer; and the processor is configured to select the first recognizer if an examination type identified by the examination information is the first type of examination, and is configured to select the second recognizer if the examination type is the second type of examination.

16. The diagnosis support apparatus according to claim 11, wherein the plurality of recognizers include a first recognizer and a second recognizer, the second recognizer having a higher sensitivity than the first recognizer or a lower specificity than the first recognizer; and the processor is configured to select the first recognizer if interpretation proficiency of a doctor or a laboratory technician, the interpretation proficiency being identified by the examination information, is lower than a threshold, and is configured to select the second recognizer if the interpretation proficiency is higher than a threshold.

17. The diagnosis support apparatus according to claim 11, wherein the plurality of recognizers include two or more recognizers machine-learned using two or more general populations including test images collected on a region-by-region basis; and the processor is configured to select a recognizer corresponding to an examination conduction region identified by the examination information.

18. The diagnosis support apparatus according to claim 11, wherein the plurality of recognizers include a first recognizer and a second recognizer whose arithmetic operation amount or arithmetic operation time is smaller or shorter than an amount or time of the first recognizer; and the processor is configured to select the first recognizer if a type of the breast image, the type being identified by the examination information, is a still image, and is configured to select the second recognizer if the type of the breast image is a moving image.

19. The diagnosis support apparatus according to claim 11, wherein the processor is further configured for performing control to display recognizer information indicating a type or a property of the recognizer selected by the processor, on a display, together with result information indicating the recognition result.

20. A diagnosis support method comprising making one computer or a plurality of computers execute steps of:

retrieving examination information relating to an examination of the subject, said examination information comprising a type of examination to be performed selected from a predetermined plurality of examination types;

based on the examination information, automatically selecting a recognizer to be used for recognition processing of a breast image showing a projection image or a section image of a breast of a subject or a recognizer that is to output a recognition result of the recognition processing, from among a plurality of recognizers comprising at least a first recognizer and a second recognizer each including a neural network, wherein the first recognizer is associated with a first type of examination and the second recognizer is associated with a second type of examination, wherein the first recognizer is a recognizer trained on a first data set to have a lower false-positive rate than the second recognizer, and wherein the second recognizer is a recognizer trained on a second data set different from the first data set to have a lower false-negative rate than the first recognizer; and with the first recognizer or the second recognizer, performing the recognition processing.

* * * * *

UNITED STATES PATENT AND TRADEMARK OFFICE
CERTIFICATE OF CORRECTION

PATENT NO. : 12,334,211 B2
APPLICATION NO. : 17/796694
DATED : June 17, 2025
INVENTOR(S) : Tetsu Hayashida et al.

Page 1 of 1

It is certified that error appears in the above-identified patent and that said Letters Patent is hereby corrected as shown below:

In the Claims

Column 18, Claim 12, Line 9, please remove the word "selects".

Signed and Sealed this
Twelfth Day of August, 2025

Coke Morgan Stewart
*Acting Director of the United States Patent and Trademark Office*